(12) United States Patent
Li

(10) Patent No.: US 7,635,433 B2
(45) Date of Patent: Dec. 22, 2009

(54) SYSTEM AND METHOD FOR FEATURE ALIGNMENT

(75) Inventor: Xiangdong Don Li, Union City, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 626 days.

(21) Appl. No.: 11/213,582

(22) Filed: Aug. 26, 2005

(65) Prior Publication Data

US 2007/0045190 A1   Mar. 1, 2007

(51) Int. Cl.
*B01D 15/08* (2006.01)
(52) U.S. Cl. .................. 210/656; 210/143; 210/198.2; 436/161
(58) Field of Classification Search .................. 210/656, 210/101, 143, 198.2; 436/161
See application file for complete search history.

(56) References Cited

U.S. PATENT DOCUMENTS

| | | | | |
|---|---|---|---|---|
| 4,772,388 | A * | 9/1988 | Allington | 210/198.2 |
| 5,730,867 | A * | 3/1998 | Drew et al. | 210/198.2 |
| 6,456,955 | B1 * | 9/2002 | Andrews et al. | 702/104 |
| 6,989,100 | B2 * | 1/2006 | Norton | 210/656 |
| 2005/0011836 | A1 * | 1/2005 | Bidlingmeyer et al. | 210/656 |

FOREIGN PATENT DOCUMENTS

| | | |
|---|---|---|
| EP | 0161672 | 11/1985 |
| EP | 161672 | * 11/1985 |
| EP | 1600771 | 11/2005 |

OTHER PUBLICATIONS

Johnson (Journal of Chromatography A 996 (2003), pp. 141-155).*
Gong (Journal of Chromatography A 1029 (Mar. 2004), pp. 173-183).*
EP Searcjh Report dated Nov. 8, 2006; 2 Pages.
Kevin J. Johnson, et al—"High- Speed Peak Matching Algorithm For Retention Time Alignment Of Gas Chromatographic Data For Chemometric Analysis"; Journal Of Chromatography A, Elsevier, Amsterdam, NL; vol. 996, No. 1-2; May 9, 2003; pp. 141-155.; XP004427349.
Fan Gong, et al—"Correction Of Retention Time Shifts For Chromatographic Fingerprints Of Herbal Medicines"; Journal Of Chromatography, Elsevier Science Publishers B. V. Amsterdam, NL, vol. 1029, No. 1-2, Mar. 12, 2004, pp. 173-183; XP004489252.
Roger Anderson, et al—"Simplex Focusing Of Retention Times And Latent Variable Projections Of Chromatographic Profiles"; Chemometrics And Intelligent Laboratory Systems, Elsevier Science Publishers B. V., Amsterdam, NL, vol. 22, No. 1, Jan. 1994; pp. 49-61; XP000414576.

(Continued)

*Primary Examiner*—Ernest G Therkorn

(57) ABSTRACT

In a system and method for feature alignment in chromatographic systems, the system runs a first sample through a first separation column. The system determines a first set of features for the first sample run. The system runs a second sample through a second separation column and detects a second set of features for the second sample run. The system estimates a systematic shift in features between the first sample run through the first separation column and the second sample run through the second separation column. The system adjusts the second set of features detected for the second sample run through the second separation column based on the estimated systematic shift to obtain a third set of adjusted features.

11 Claims, 3 Drawing Sheets

OTHER PUBLICATIONS

"Retention Time Locking With The G1701BA MSD Productivity ChemStation"; Internet Citation (Online) Dec. 1998, XP002293693, Retrieved from the Internet: URL:www.chem.agilent.com/scripts/library.asp?>; Retrieved Aug. 24, 2005 . . . pp. 1-6. XP002293693.

Jenny Forshed, et al—"Peak Alignment of NMR Signals By Means Of A Genetic Algorithm"; Analytica Chimica Acta; Jul. 8, 2003, vol. 487, No. 2, pp. 189-199, XP002406120.

* cited by examiner

SYSTEM AND METHOD FOR FEATURE ALIGNMENT

BACKGROUND

Chromatography is a process that provides for the physical separation, quantification and identification of various analytes in a sample in a single analysis. A chromatography system comprises a number of components, including a separation column that separates the sample into its individual components as the components are passed through the column by a mobile phase. The separation column includes an inlet portion that acts as the interface for input of the sample into a separation column. The mobile phase provides a carrier fluid and driving force to move the components of the sample from the inlet portion of the column to the outlet portion, with the separation of the components dependent on their interactions with an immobilized liquid or solid material within the column (stationary phase) and the mobile phase. The system also includes a detector that detects and measures components as they exit the separation column at different times. The components of the sample are measured based on the relative timing of the detection of those components at the outlet of the separation column. The exit time of a component is defined as the retention time for that component. For chromatographic methods involving large numbers of components, a significant amount of work is required to determine the retention time of each individual component during chromatographic method development. Also significant is the amount of work needed to correlate data generated on multiple instruments performing the same analysis, and on the same instrument for different samples, even for a small number of components.

In gas chromatography (GC) the carrier fluid is a gas or a supercritical fluid which acts similarly to a gas in the system. In liquid chromatography (LC) the carrier fluid is a liquid. In both gas and liquid chromatography systems a portion of the sample is injected into a steady flow of the carrier fluid at the input portion of the column, and the components are passed through the stationary phase material in the column. At the output portion of the column the individual components exit the column separately and are measured by the detector as a function of intensity (or quantity) and as a function of the time of exit relative to the sample entering the column. The column is monitored for effluent using a detector that provides a pattern of retention times which, by calibration or comparison with known samples, can be used to identify the components of the sample chemically and quantitatively. Additional components of a chromatography system include an injector with a mixing chamber for introducing the sample into the carrier fluid at the inlet portion, fluid controls, and a computer for processing and displaying the output of the detector. The display generally identifies the output of the column formatted according to retention times.

The various parts of a chromatographic system are not static, but include systematic changes with time and use. Such changes, for example, result from environmental or other factors, including changes that may affect certain parts of the system, such as, for example, the column, the stationary phase and the detector, to name a few. These changes can also affect other parts of the chromatographic system including, for example, the mobile phase, carrier fluid and the sample.

In addition to the systematic changes, a chromatographic system can experience random changes that are not predictable. These changes, for example, may result from measurement errors, improper calibration or external unpredictable stimuli, to name a few.

It is well understood that the retention time of a particular compound as measured in a first run through a chromatographic system cannot be repeated exactly in a subsequent run. The retention times vary from run to run even under the same laboratory protocols and even where special care is given to maintaining a static and controlled environment. This poses a big challenge when trying to correlate a feature in one chromatography data set with the feature of the same compound in another chromatography dataset, such as, for example, a liquid chromatography-mass spectrometry (LC-MS) dataset.

One obvious solution to this problem is to correlate corresponding features in two different datasets when both their m/z values and retention times are close to one another. The term m/z means the ratio of charge to mass of the ion detected, where z is often unity but can be a larger integer. The m/z value is used to measure peaks resulting from the detection of components of a sample that has been run through a chromatography system. This approach is prone to errors generally, and even more so when working with complicated sample chemistry. To compensate for the deviations that are usually encountered, and to cover all possible retention time deviations, a sufficiently large tolerance window can be chosen to compensate for the deviations which allows correlations to be made even when the peaks are not near one another but nevertheless fall within the tolerance window. This method of compensation, however, can introduce mismatches and errors with respect to the datasets that are output from the chromatography system. These mismatches and errors can become even more significant as the complexity of the datasets increase. The result is that features corresponding to different compounds are mistakenly correlated due to the large tolerance window.

SUMMARY OF THE INVENTION

The present invention provides for a more accurate comparison of features of different samples or of the same sample from different runs, including, for example, as represented by retention times from different runs of the same or different samples, and a reduction of the probability and likelihood of a mismatch or mistaken correlation of features, such as, for example, retention times for compounds from different datasets by removing deviations, such as, for example, retention time deviations. For example, by removing retention time deviations the system provides for retention time shift correction.

A method for feature alignment in chromatographic systems, comprising: running a first sample through a first separation column; determining a first set of features for the first sample run; running a second sample through a second separation column; detecting a second set of features for the second sample run; estimating a systematic shift in features between the first sample run through the first separation column and the second sample run through the second separation column; and adjusting the second set of features detected for the second sample run through the second separation column based on the estimated systematic shift to obtain a third set of adjusted features.

A chromatographic system for providing feature alignment, comprising: a separation column, having an inlet portion for insertion of a sample, and an outlet portion; a detector that detects and measures a component of the sample as it reaches the outlet portion; and a processor coupled to the detector, that processes an output of the detector and determines a feature for the component of the sample, wherein the processor estimates a systematic shift in the feature of the component of the sample and adjusts the feature for the component of the sample based on the estimated systematic shift in the feature.

A chromatographic system for providing feature alignment, comprising: a separation column, having an inlet portion for insertion of a first sample and second sample, and an outlet portion; a detector that detects and measures a component of the first sample as it reaches the outlet portion and a component of the second sample as it reaches the outlet portion; and a processor coupled to the detector, that processes an output of the detector and determines a feature for the component of the first sample and a feature for the component of the second sample, wherein the processor estimates a systematic shift in the feature of the component of the second sample and adjusts the feature for the component of the second sample based on the estimated systematic shift in the feature.

Retention time shift correction is accomplished by dividing the retention time deviations into separate components. One component corresponds to deviations relating to systematic sources, such as, for example, those caused by variations in gradient rate, solvent composition, and column aging. For a given retention time, compounds would shift substantially the same amount as a result of the systematic deviation. Another component corresponds to random deviations, such as those due to component interaction, minor local damage of the column, minor pump malfunction, measurement error.

Generally, the systematic deviations result in a steady change in retention time, varying slowly over time. The relative retention-time change between two runs can be estimated by mathematical modeling, for example, using polynomial regression, as long as the two runs in comparison have many common components. When more than two runs are analyzed, we can select one run as the reference and retention-time shifts of all other runs can be estimated relative to the reference.

The random deviations do not follow a recognizable pattern and are therefore not determinable. However, by estimating and removing the systematic deviations, the present invention is able to reduce the overall retention time deviation thereby ensuring that the retention times for corresponding components fall closer together from run to run. This allows for a reduction in the size of the tolerance window and reduces the possibility of mismatches (or mistaken correlations).

Corrections may be made to the feature measurement, such as, for example, retention time measurement, that is output from the system after locating matching features, such as, for example, by identifying peaks, from the two runs and estimating the systematic deviations between the features, such as, for example, the peaks, from the two runs. There corrections may be accomplished, for example, using regression analysis, and the two sample runs may then be compared for purposes of correlation using a smaller tolerance window to provide more accurate results and reduce mismatches.

BRIEF DESCRIPTION OF THE DRAWINGS

FIG. 2a shows a diagram of a chromatography system according to an embodiment of the present invention.

FIG. 2b shows a diagram of a separation column for the chromatography system of FIG. 2a.

DETAILED DESCRIPTION

The term alignment refers to correlating or associating two features of the same compound or same part of a compound, which are present in two runs, respectively.

The term feature refers to a physical or chemical or biological property of a compound or part of a compound, such as, for example, molecular weight, atomic mass, chemical structure, that can be represented by particular physical parameters, such as, for example, as presented in a LC-MS dataset with a representative retention time and m/z.

The term retention time refers to the amount of time that a given compound or part of a compound takes to pass through a chemical analysis system, such as, for example, a chromatography system.

The term systematic shift refers to deviations relating to systematic sources, such as, for example, those caused by variations in gradient rate, solvent composition, and column aging.

When determining whether two features from two separate runs correspond to the same chemistry identity, a comparison must be made between their retention times from the chromatography system. In a first example, where a first sample and a second sample both containing compound X are to be run through a chromatography system, we can refer to the run relating to the first sample as Run A and the run relating to the second sample as Run B. The retention time for compound X resulting from Run A is referred to as $T_A$ and the retention time for compound X resulting from Run B is referred to as $T_B$.

The retention time deviation times for compound X between Run A and Run B is represented by the following formula:

$$dT = T_B - T_A \quad [1]$$

The retention time deviation as shown in Formula 1 is a function of retention time T and can be represented as follows:

$$dT = dT(T) \quad [2]$$

The retention time deviation as shown in Formula 2 may be separated into two components as represented by the following formula:

$$dT = dT_S + dT_R \quad [3]$$

The retention time shift correction according to the present invention is accomplished by dividing the retention time deviations into these separate components. One component from Formula 3, $dT_S$, corresponds to deviations relating to systematic sources, such as, for example, those caused by variations in gradient rate, solvent composition, and column aging. This component is systematic for all the chemical compounds.

Figure 1:
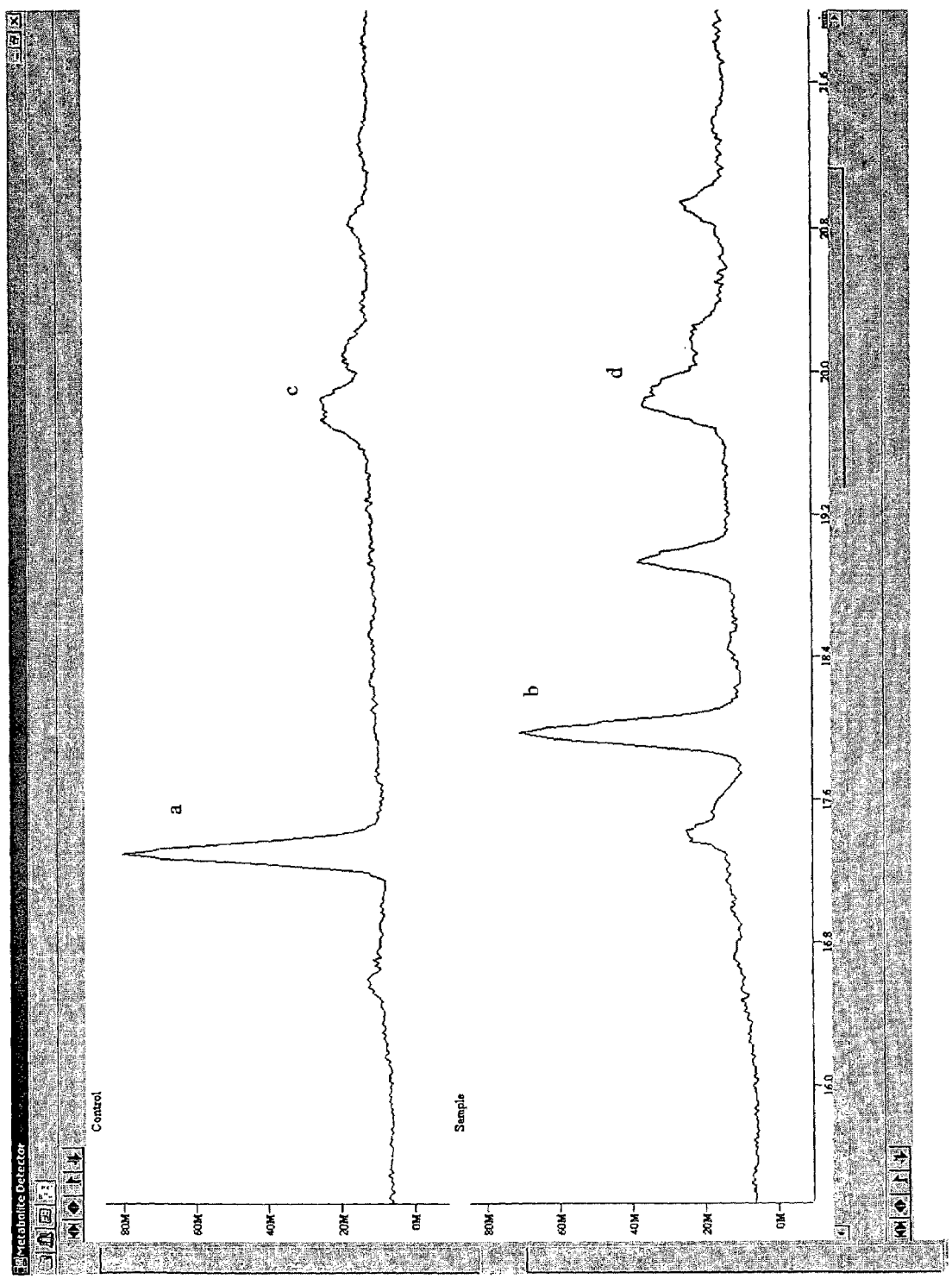
FIG. 1 shows a graph of systematic deviation over time between two runs.

Generally, the deviations relating to systematic sources result in a gradual change over time. Thus, generally, $dT_S$ can be represented as a smooth function of T. For example the graph in FIG. 1 shows an extreme but realistic retention time shift between two runs, represented by the top and bottom chromatograms, respectively. At an earlier portion of the time spectrum, the compounds making up the sample arrive systematically later for the bottom run than the top run (see portions a and b). The amount of the shift changes slowly with the time. At the later portion of the time spectrum, the retention times of the bottom run catch up with the top run (see portions c and d). For systematic deviations, compounds arriving at the similar retention times have the similar retention time shift between runs. Thus $dT_S(T)$ can be estimated statistically, for example, by using polynomial regression. First, for each compound having retention time t in Run A, we search for a counter part compound in Run B in the neighborhood of t using a relatively wide tolerance window. For example, where LC-MS data is used, the same m/z is required for the match. In systems using non LC-MS data, additional constraints may be required for the match. If a counter part is found, the retention time difference can be measured and used in the regression. If a counter part is not found the value is ignored for purposes of the regression At this stage, the effect of mismatches on the regression result $dT_S(T)$ is minimal, because the regression result is sensitive statistically only to the systematic distribution of the data.

Combining Formula 1 and Formula 3 gives us the following:

$$dT_S + dT_R = T_B T_A$$

$$dT_R = (T_B - dT_S) - T_A$$

Because the deviation that remains after determination of the systematic deviation using the mathematical model is deviation of a random nature for which the system cannot compensate, the variable $dT_R$ in the formula becomes the residual deviation as represented by the following formula:

$$dT = (T_B - dT_S) - T_A \quad [4]$$

The residual deviation, dT', is generally smaller than the original deviation $d_T$. Therefore, when attempting to correlate the retention times for compounds from from Run A to the retention times for compounds from Run B, a smaller tolerance window may be used, thereby reducing the probability of mismatches or mistaken correlations.

Figures 2A, 2B:
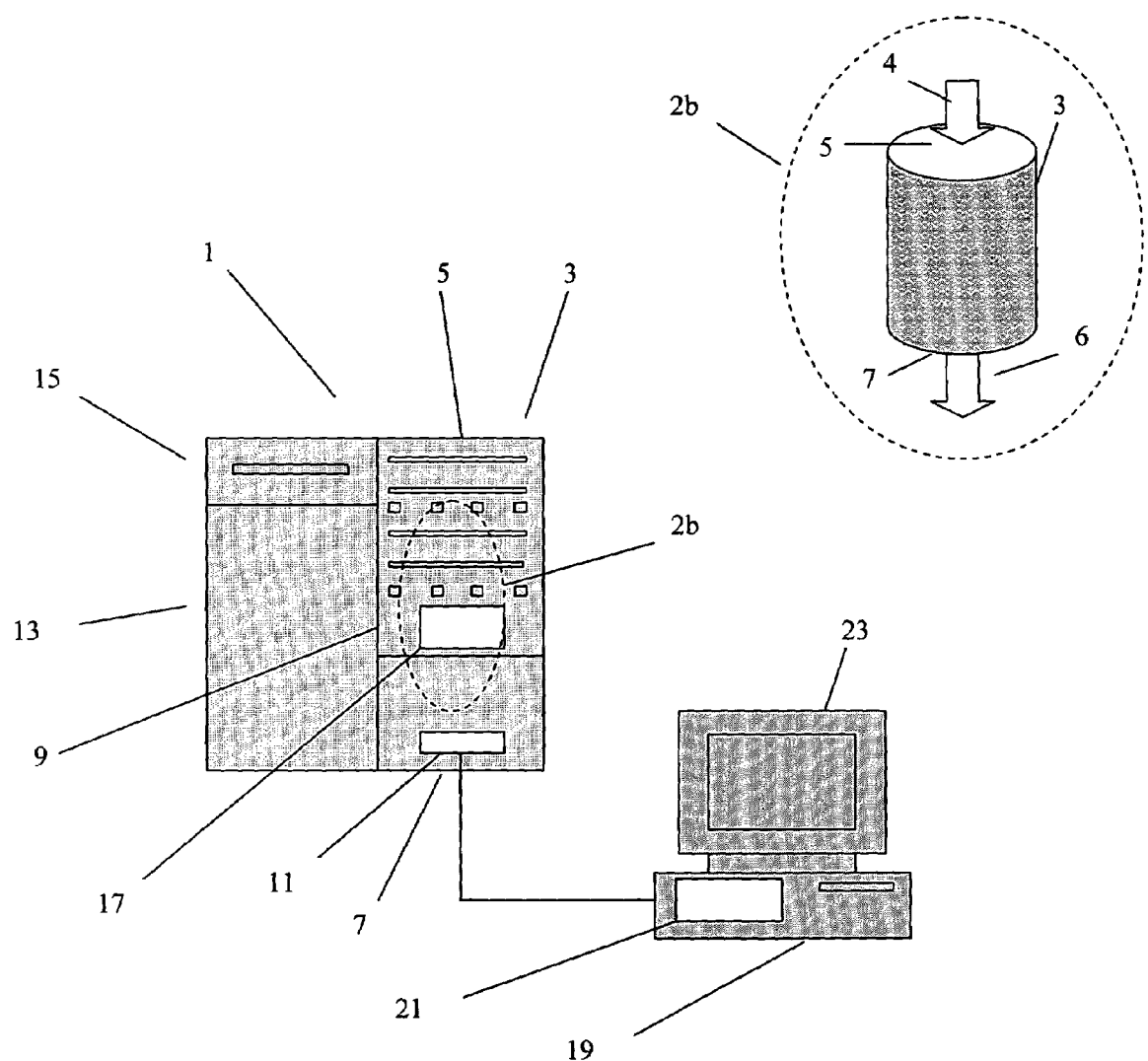

In FIG. 2a there is shown a diagram of a chromatography system according to an embodiment of the present invention. The chromatography system 1 includes a separation column 3, having an inlet portion 5 that acts as the interface for input of a sample into the separation column 3, and an outlet portion 7 that provides an outlet for sample. The separation column, with an arrow 4 showing the direction of flow to the inlet portion 5 and an arrow 6 showing the direction of flow from the outlet portion 7 is shown in more detail in FIG. 2b. The separation column 3 separates the sample into its individual compounds as the sample is passed through the column by a mobile phase. The mobile phase provides a carrier fluid (not shown) that passes through the separation column 3 and provides a driving force to move the compounds making up the sample from the inlet portion 5 of the separation column 3 to the outlet portion 7. The separation of the compounds making up the sample is dependent on their interactions with an immobilized liquid or solid material within the column, the stationary phase 9, and the mobile phase.

The chromatography system 1 also includes a detector 11 that detects and measures each of the compounds making up the sample as they reach the outlet portion 7 and exit the separation column 3 at various times. An injector 13 coupled to a mixing chamber 15 is located near the inlet portion 5. The injector 13 is used to introduce the sample into the mixing chamber 15 for dispersing the sample in the carrier fluid to generate the mobile phase. Upon dispersion of the sample in the carrier fluid, the carrier fluid is released at the inlet portion 5 and moves through the separation column 3 toward the outlet portion 7.

Included as part of the chromatography system 1 may be fluid controls 17 that are used to control and adjust the mobile phase and its progress through the separation column 3. The chromatography system 1 also includes a processor or computer 19 coupled to the detector 11, that processes the output of the detector 11 and controls the various functions of the chromatography system 1. The processor or computer 19 includes a module 21 that can be implemented as hardware, software or a combination of hardware and software, that is used to estimate systematic shift in retention times and adjust the retention times based on the estimated shift. The chromatography system 1 may include a display device 23, such as, for example, a CRT, LCD or LED monitor, coupled to the processor or computer 19 that is used to view the output of the chromatography system 1, including the retention times, and other system functionality. The display device 23 generally identifies the output of the separation column 3 formatted according to retention times.

Figure 3:
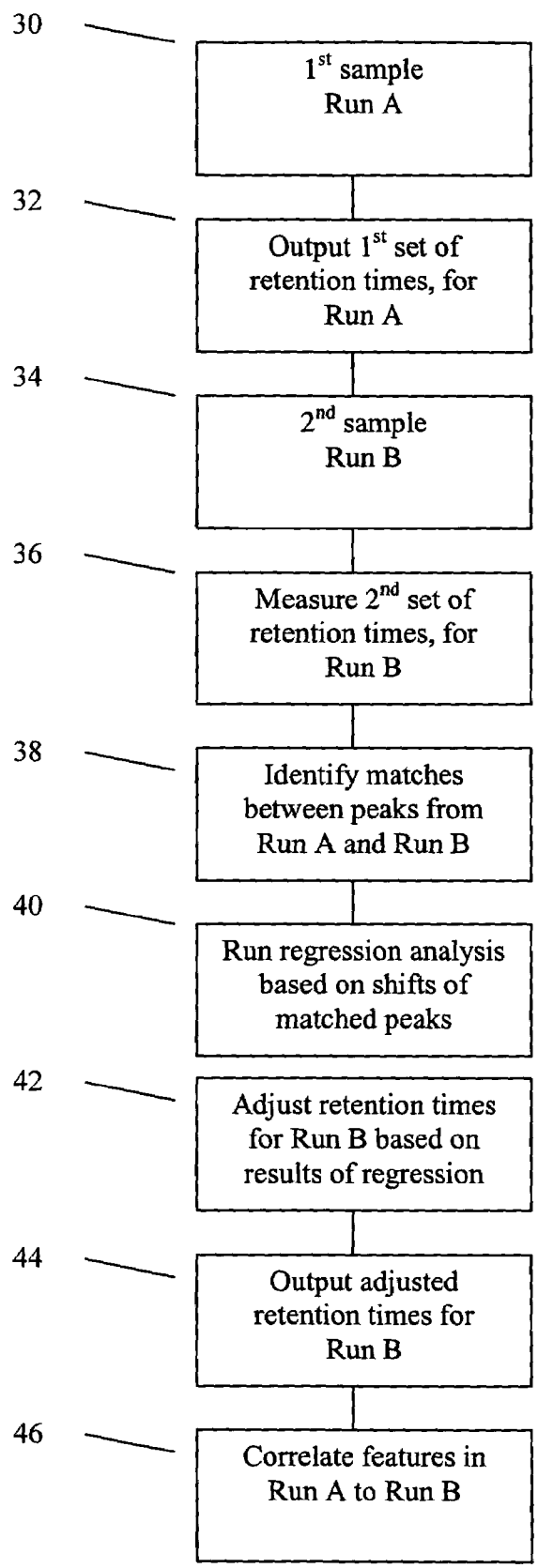
FIG. 3 shows a flow diagram of a correlation process according to a first embodiment of the present invention.

Having discussed the apparatus a description of a method according to an embodiment of the present invention is now in order. Looking now to FIG. 3, there is shown a flow diagram of a correlation process according to a first exemplary embodiment of the present invention. In step 30, a first sample is run through a LC-MS chromatography system for a first run, Run A.

In step 32, a first set of retention times are output from the LC-MS chromatography system for the first sample from Run A. In step 34, a second sample is run through the LC-MS chromatography system for a second run, Run B. In step 36, a second set of retention times are measured for the second sample from Run B. In step 38, the LC-MS chromatography system attempts to identify a match for each of the peaks from Run A with each of the peaks from Run B, to the extent such matches exist, using a relatively wide tolerance window. In step 40, the LC-MS chromatography system runs a regression analysis based on the shifts of each of the matched peaks from Run A to Run B. In step 42, the LC-MS chromatography system adjusts the retention times calculated for the second sample from Run B based on the results of the regression analysis. In step 44, the adjusted set of retention times for the second sample from Run B are output from the LC-MS chromatography system. In step 46, the system, operator or analyst correlates a feature in Run A to a feature in Run B based on a narrower tolerance window than previously used while reducing the probability of mismatches and mistaken correlations.

What is claimed is:

1. A method for feature alignment in chromatographic systems, comprising:

running a first sample through a first separation column;

determining a first set of features and a first set of retention times for the first sample run;

running a second sample through a second separation column;

detecting a second set of features and a second set of retention times for the second sample run;

identifying matches between said first set of feature and said second set of features;

estimating a systematic shift in features between the first sample run through the first separation column and the second sample run through the second separation column, wherein said estimating comprises performing a polynomial regression calculation on respective retention times from said first and second sets of retention times corresponding to said matches; and adjusting the second set of features detected for the second sample run through the second separation column based on the estimated systematic shift to obtain a third set of features, wherein the third set of features are adjusted features having a third set of retention times, wherein features of said third set that match features of said first set have retention times that differ from said retention times of the matching features in the first set by only residual deviation not caused by systematic deviation.

2. The method according to claim 1, wherein the first sample and the second sample are each a portion of the same sample.

3. The method according to claim 1, wherein the first separation column and the second separation column are the same separation column.

4. The method according to claim 1, wherein the first set of features, the second set of features and the third set of adjusted features are each relative features.

5. The method according to claim 1, wherein the systematic shift is estimated based on at least one of gradient rate, solvent composition, and column aging.

6. The method according to claim 1, wherein the adjusting of the second set of features to obtain the third set of adjusted features is accomplished by subtracting the estimated systematic shift from the second set of features detected for the second sample run through the second separation column.

7. The method according to claim 1, wherein the first set of features and the third set of adjusted features are each output in printed form.

8. The method according to claim 1, wherein the first set of features and the third set of adjusted features are each output to a display device.

9. The method according to claim 1, further comprising correlating the first set of features with the third set of adjusted features.

10. The method according to claim 1, further comprising outputting the first set of features for the first sample run and the third set of adjusted features.

11. The method according to claim 1, wherein the third set of adjusted features is represented by a set of retention times.

* * * * *

UNITED STATES PATENT AND TRADEMARK OFFICE
CERTIFICATE OF CORRECTION

PATENT NO. : 7,635,433 B2 Page 1 of 1
APPLICATION NO. : 11/213582
DATED : December 22, 2009
INVENTOR(S) : Xiangdong Don Li It is certified that error appears in the above-identified patent and that said Letters Patent is hereby corrected as shown below:

In column 8, line 17, in Claim 11, delete "a set" and insert -- a third set --, therefor.

Signed and Sealed this

Ninth Day of November, 2010

David J. Kappos
*Director of the United States Patent and Trademark Office*